United States Patent [19]

Lostia et al.

[11] 4,031,201
[45] June 21, 1977

[54] FIBRES INCORPORATING ANTIBODIES, ANTIGENS AND ANTISERA, METHOD FOR THEIR PREPARATION AND THEIR USE

[75] Inventors: Onofrio Lostia; Francesco Bartoli, both of Rome, Italy

[73] Assignee: Snam Progetti S.p.A., Milan, Italy

[22] Filed: July 29, 1975

[21] Appl. No.: 599,993

[30] Foreign Application Priority Data

July 31, 1974 Italy .................................. 52379/74

[52] U.S. Cl. .................................. 424/27; 424/12; 424/14; 424/16; 424/85; 424/88
[51] Int. Cl.² .................. A61K 9/70; A61K 39/00; A61K 39/12
[58] Field of Search ................ 424/12, 16, 14, 27, 424/85, 88, 78, 81; 128/335.5

[56] References Cited

UNITED STATES PATENTS

| | | | |
|---|---|---|---|
| 3,645,852 | 2/1972 | Axen et al. | 195/68 |
| 3,674,901 | 7/1972 | Shepherd et al. | 128/335.5 |
| 3,700,609 | 10/1972 | Tregear et al. | 260/2.5 R |
| 3,711,574 | 1/1973 | Jaworek et al. | 260/878 R |
| 3,715,277 | 2/1973 | Dinelli et al. | 195/63 |
| 3,806,417 | 4/1974 | Beaucamp et al. | 195/63 |
| 3,843,324 | 9/1972 | Edelman et al. | 23/230 B |

*Primary Examiner*—Sam Rosen
*Attorney, Agent, or Firm*—Shlesinger, Fitzsimmons & Shlesinger

[57] ABSTRACT

Artificial fibres containing antibodies, antigens or antisera are prepared by emulsifying the substances to be incorporated in the interior of the fibres and spinning the emulsion thus obtained through a spinneret immersed in an appropriate coagulation bath, when the coagulation liquor and the solvent(s) have been removed, a fibre is obtained which can be used in many fields wherever it is required to remove antibodies, antigens or antisera from certain substances. The fibres thus obtained could also be used for chromatographical methods of the affinity chromatography type.

4 Claims, 1 Drawing Figure

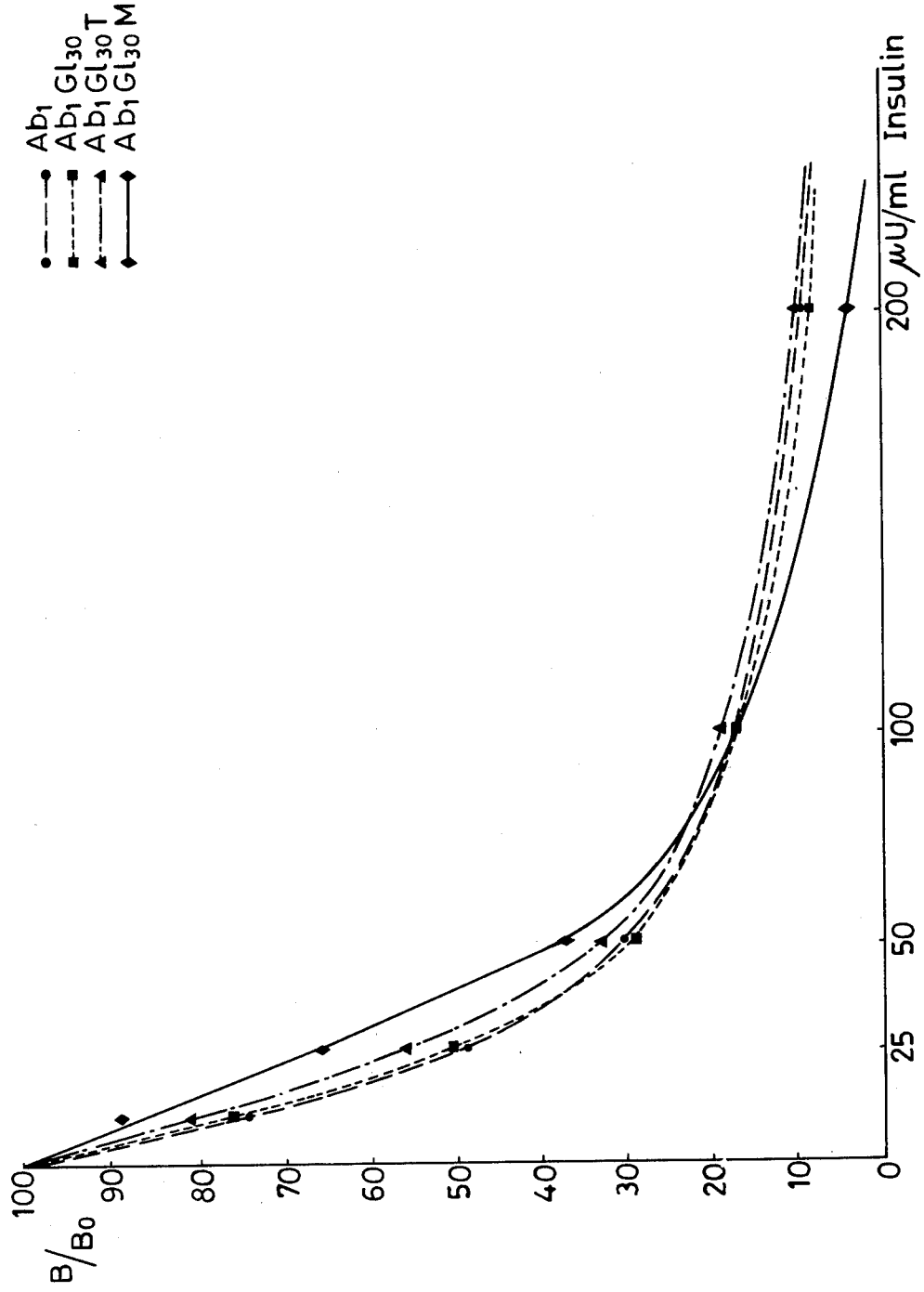

FIBRES INCORPORATING ANTIBODIES, ANTIGENS AND ANTISERA, METHOD FOR THEIR PREPARATION AND THEIR USE

This invention relates to fibres which incorporate antibodies, antigens, antisera, as such or polymerized, and also to the method for incorporating such substances.

It is known that the term "antibody" relates to substances of a proteinic nature which are formed in vertebrates by particular cells (plasma cells) in response to the administration of an antigen, and which specifically react with the latter.

The study of the reactions between antigen and antibody has a considerable theoretical importance from the point of view of gaining a better understanding of the interaction between the molecules, but it has also a practical importance in that it can supply increasingly sophisticated methods for the diagnosis of infectious diseases and the identification of infecting agents. To this end one component is analyzed, the other being known. As regards antigens and antibodies there have been disclosed some methods of insolubilization by means of chemical bonds between the said products and polymeric materials insoluble in an aqueous solvent.

However, these preparations have the drawback of continuous contact with the external atmosphere, of possible dispersion in the reaction mass and thus possible pollution of the final product itself. In addition, it should be observed that the occurrence of chemical bonds may influence the chemical nature of the substance itself, with possible detrimental consequences for its activity.

On the other hand, it is likewise known that it is possible to prepare porous fibres which have enzymes embedded therein, the latter retaining, by their being so immobilized, their catalytic properties, while at the same time the enzyme is prevented from escaping and being dispersed in the reaction mass and thus contaminating the reaction product. The filamentous structures which can be used and the method of embedding the enzyme are those described in the Italian Pat. No. 836,462, according to which the enzyme-embedding fibres can be prepared starting from solutions of polymers capable of giving fibres in which there are dispersed enzymic preparations in the form of very tiny droplets of the order of magnitude of the emulsions. The emulsion thus obtained can be spun either in wet or dry conditions to give a fibre which has in its interior extremely small hollows in which the enzymes are located and are excluded from the ambient atmosphere by a very thin membrane, the latter preventing the enzyme from escaping and being dispersed in the reaction mass, while nevertheless allowing the enzyme to exert its catalytic action.

It has now been found that, by employing methods similar to those used for enzymes, it is possible to incorporate within porous structures antigens, antibodies, antisera, either as such or polymerized, and that the preparations thus obtained do not exhibit the drawbacks referred to above and this without any prejudicial decrease of activity towards the native proteins.

The structures obtained in this way possess high activity on account of the high surface area-to-volume ratio, the method for their manufacture is very simple and inexpensive to carry out and, moreover, affords the possibility also of embedding substances that do not possess a high degree of purity.

The filamentous structure incorporating antibodies, antigens and antisera according to the present invention find application in several fields in which the principle of reciprocal specific reactivity is always exploited. Thus, for example, as regards antisera and antibodies, such fibers can be used to remove from the outside ambience antigens, aptenes and substances conjugated with proteins and/or polypeptides, or, alternatively, using embedded polymerized antigens, it is possible to remove more or less specific antibodies. Yet again, the above mentioned filamentary structures can be used to carry out extractions of industrial interest by selective fixing and possible detaching of the fixed substance (antigens, antibodies, and so forth), as for example the extraction of enzymes such as amylase, protease, invertase and the like. It is also possible to use such fibres in chromatographic methods and more particularly in affinity chromatography, for example to separate iso-enzymic substances of the cholinesterase type.

The difference in molecular weight between the proteins embedded in microcavities in the interior of the fibre and the substances to be bonded thereto must be sufficient to allow diffusion into the interior of the fibre of the substance(s) to be bonded until the latter reach(es) the substance having the greater molecular weight, which remains occluded in the fibre owing to its greater molecular weight.

The method for the preparation of the filamentary structures mentioned above is carried out, as mentioned hereinbefore, in a manner similar to that for enzyme embedding.

More particularly, the method comprises the following stepwise sequence:

a. preparation of the substance to be embedded, with verification of the aspecific fixing on the fibre material and also of lack of inactivation or of non-significant inactivation after treatment with the spinning solvents.
b. dissolution or suspension of the substance (a) in water or in a water-glycerol mixture.
c. addition of the solution or suspension (b) to a polymer in solution.
d. stirring until a homogeneous emulsion is obtained.
e. spinning the emulsion (d) through a spinneret immersed in a coagulation bath.
f. removal of the coagulation liquor and the solvent of the polymer from the fibre by treatment in a stream of air or other gas, if necessary.

The spinning conditions and the characteristics of the polymers which can be used are those already specified in the aforementioned Italian Patent.

Among the polymeric materials which are preferred for the preparation of the fibres according to the invention, mention can be made of the cellulose polymers, the esterified cellulose polymers, as well as the etherified and nitrated polymers of cellulose, and especially the cellulose triacetate polymers. Other polymers which can be employed are polyethylene, the polyamides, the polymers or copolymers of acrylonitrile, butadiene or isoprene, the acrylates, methacrylates, the vinyl esters, the vinyl chlorides, the polymers or copolymers of vinylidene chloride, styrene, vinylbutyrate, gammamethyl glutamate and the like.

In any case, all the operative details will become more clearly apparent from the ensuing illustrative examples, the invention being not limited in any wise thereby.

EXAMPLE 1

I. Preparation of Antisera

The antisera are obtained in Guinea pigs, rabbits or other animals.

The substance against which it is desired to obtain the antiserum (conjugated antigen or aptene) is admixed with complete Freund adjuvant and injected in the medial face of the haunch of the rear leg of the animal. After 15 and 30 days the injection is repeated with an equal dosage of the immunizing agent (antigen plus Freund adjuvant) and, after 15 more days a further immunization with half-dosage is carried out. Then, at 15-day intervals, intracardial blood samplings are taken and on the serum obtained the antibody titre is determined. This is determined by making serial dilutions of the antiserum with Veronal buffer, 0.02 molar, at pH=8.4, containing 0.5% of human seroalbumin (h.s.a.) and 0.5% of normal serum.

With radioimmunological assay methods (RIA) the dilution is found to which corresponds a ratio B/F = 1. Again with RIA methods, the affinity of the antiserum obtained is also determined.

II. Preliminary tests

A. Aspecific fixing tests
B. Antiserum inactivation tests by treatment with the solvent used for the spinning

A. Aspecific fixing test

In plastic tubes weighing was made of 50 mg of a fibre as obtained after the process of spinning, coagulation and solvent removal.

The fibre did not contain antiserum or other sequestering agents but only an admixture of water and glycerol.

Three sets of small tubes were prepared, namely:
a. 50 mg fibre plus 2.0 ml phosphate buffer (as the blank)
b. 50 mg fibre plus 1.5 ml phosphate buffer plus 0.5 ml labeled antigen (Ag-$I^{125}$)
c. 50 mg fibre plus 0.5 ml phosphate buffer plus 1.0 ml of a solution of bovine seroalbumin (BSA), 5th fraction at 2.5% concentration in phosphate buffer plus 0.5 ml labeled antigen (Ag-$I^{125}$).

0.04 molar phosphate buffer was used, having a pH of 7.4 and containing 0.5% of BSA.

The labeled antigen was Insulin-$I^{125}$ with a specific activity of 100 $\mu$ C per microgram which was added in the proportion of 0.1 $\mu$ C per 50 mg of fibre.

Digoxin-$I^{125}$ was also used in solution of ethanol having an activity of 0.25 $\mu$ C per 0.5 ml and of this solution there was added 0.025 $\mu$ C per 50 mg of fibre.

Both solutions were brought to the desired dilution with phosphate buffer.

A portion of the fibres, prior to addition of the labeled antigen, were placed into contact for 1 hour with the solution containing 2.5% of BSA.

The contact times of the fibres with the labeled antigen varied from 40 minutes to 48 hours.

The activities of the small tubes containing the fibres were measured with a gamma-counter.

On completion of the contact time, the fibres were washed five times with 2 ml of phosphate buffer each time, then the residual radioactivity was measured with a gamma counter.

Subsequently, the fibres were washed five additional times, again with 2 ml phosphate buffer, and the radioactivity was measured. Then the fibres were placed into contact with 2 ml phosphate buffer with stirring at 37° C for 17 hours and the residual radioactivity was again measured; this step was repeated twice more. It was found that:
a. The radioactivity associated with the fibres is gradually increased when the time of contact with the labeled antigen is from 40 minutes to 48 hours.
b. Pre-incubation for 1 hour with 2.5% BSA causes the quantity of radioactivity associated with the fibre to be diminished.
c. With regard to the radioactivity added to the small tubes, it was noted that, owing to the effects of the washings, the radioactivity is decreased as the number of the washings is increased, and also as the time of contact of the fibre with the washing buffer is increased; a small percentage of radioactivity is retained, also, after the washing steps described above.

Thus, it was concluded that, like the great majority of materials, the fibre also adsorbed in an aspecific manner a small portion of the radioactivity present in the preparation of the labeled antigen and that such adsorption was caused to decrease by the BSA, which saturated a portion of the receptor sites located in the fibre.

B. Antiserum inactivation tests by treatment with the solvents used for the spinning Use was made of two small flasks of an anti-insulin antiserum, as supplied in commercial radioimmunoassay kits (porcine antiserum anti-insulin, obtained in Guinea pigs) and to each tube was added 5 ml of double-distilled water, thus obtaining 10 ml of a solution of antiserum anti-insulin which was called $Ab_2$. There were then prepared 20 ml of an admixture of water and glycerol (40:60) (v / v) which was called $Gl_{60}$.

There were next prepared the following mixtures:

| | | |
|---|---|---|
| a) | 2.5 ml | $Ab_2$ |
| | + 2.5 ml | distilled water |
| | 5.0 ml | $Ab_1$ |
| b) | 7.3 ml | $Ab_2$ |
| | + 7.3 ml | $Gl_{60}$ |
| | 14.6 ml | $Ab_1Gl_{30}$ |
| c) | 5 ml | $Ab_1Gl_{30}$ |
| | + 32.1 ml | methylene chloride |
| | 37.5 ml | | of two phases kept in good contact by stirring for 15 minutes at 0° C; then, after centrifuging at room temperature, the aqueous phase was removed, and from it the methylene chloride was stripped with a nitrogen stream. There were thus obtained 5 ml of a solution indicated as $Ab_1Gl_{30}M$.

| | | |
|---|---|---|
| d) | 5 ml | $Ab_1Gl_{30}$ |
| | + 2 ml | toluene |
| | 7 ml | | of two phases kept in good contact with stirring for 30 minutes at room temperature. After centrifuging at room temperature, the aqueous phase was taken off and from it the toluene was removed by a nitrogen stream. There were finally obtained 5 ml of a solution indicated as $Ab_1Gl_{30}T$.

With the usuasl RIA methods calibration curves were plotted in the range of concentrations from 0 to 200 $\mu$ U/ml of standard human insulin, utilizing the antiserum as treated in the four different ways listed above and indicated previously as:

$Ab_1$
$Ab_1Gl_{30}$
$Ab_1Gl_{30}M$
$Ab_1Gl_{30}T$

From the annexed calibration curves (FIG. 1) it is apparent that, in practice, there is no decrease in the bonding capacity of the antibody as a result of the treatment of the antiserum with the solvents used in the spinning.

III. Preparation of the Fibres 200 mg of cellulose triacetate (Fluka) are dissolved in 2.65 g of methylene chloride (reagent grade, Carlo Erba) at room temperature.

The product to be embedded is dissolved or dispersed in water or admixtures of water and glycerol.

0.4 ml of the aqueous medium is added to the solution of the polymer which has previously been cooled to 0° C. Stirring is effected until a homogeneous emulsion is obtained; this is then allowed to stand for 20 minutes.

This preparation is made in a glass cylinder the top of which is connected to a nitrogen cylinder, the bottom of the glass cylinder terminating in a spinneret immersed in a coagulation bath containing toluene.

By causing a nitrogen pressure, the emulsion emerges from the spinneret and, passing into the toluene bath, is coagulated. The resulting filament is collected on a roll and then treated with an air stream so as to remove both toluene and methylene chloride.

IV. Embedding the Anti-insulin Antibody

With the methods described above, there was prepared, in Guinea pigs, an anti-insulin antiserum, the antibody titre of which was found to be 150,000.

To 0.2 ml of this antiserum there was added 0.15 ml of 0.02 molar Veronal buffer at pH 8.4, containing 0.5% of human seroalbumin, and 0.15 ml of glycerol (reagent grade, C. Erba).

0.4 ml of this solution was added to the polymer according to the preparation conditions of the fibres as described previously.

With the same apparatus there was performed the spinning of a control fibre, in which, in the place of 0.2 ml of antiserum solution use was made of 0.2 ml of 0.02 molar Veronal buffer of pH 8.4, containing 0.5% of human seroalbumin. Into small plastic tubes of the kind used for radioimmunoassay, assays there were placed different quantities of fibre as reported in TABLE 1, wherein:

a. is the series of control fibres
b. is the series of anti-serum containing fibres, as obtained from the spinning run.
c. is the series of anti-serum containing fibres which, on completion of the spinning process, have been stored in the 0.02 molar Veronal buffer, pH = 8.4, containing 0.5% of human seroalbumin and washed five times with 2 ml of Veronal buffer before starting the test.

To each small tube there was added:

1.6 ml of 0.04 molar phosphate buffer, pH = 7.4, containing 0.5% of bovine seroalbumin.

0.2 ml Insulin-$I^{125}$ with a specific activity of 100 $\mu$ Ci/microgram and, with a dilution which adjusted the activity, as measured on the day of preparation, to 0.01 $\mu$ Ci/0.1 ml.

0.2 ml human Insulin, standard, at a concentration of 200 $\mu$ U/ml.

After mixing, the small tubes were placed in a 4° C cabinet for 24 hours. Then, from each small tube there was taken off 1.5 ml of the solution, the radioactivity of which was measured with a gamma counter (Packard Model 256) having an efficiency of 54% for $I^{125}$.

The fibres were washed three times with 2 ml of phosphate buffer whereafter the radioactivity fixed by the fibres was measured with a gamma counter as aforesaid. On the same fibre samples there were repeated the additions of the reagents (buffer, Insulin $I^{125}$, standard insulin), the washings and the radioactivity readings, four more times.

It should be noted that Insulin $I^{125}$ as used as labeling compound does not exceed 5% of the standard human insulin used as carrier. The results obtained are tabulated in TABLE 1 where it can be seen that, whereas in the control fibres not containing antibodies the fixing of insulin, which will be called aspecific, reaches a peak value in the first test and is maintained virtually constant in the subsequent tests, in the fibres which have the antibody embedded therein, the fixing of insulin is increased every time the addition of the reagents is repeated.

Since the control fibre was prepared under very much the same conditions as the antibody-embedding fibre, the behavioural difference must be attributed solely to the formation of the antigen-antibody bond in the interior of the fibre between the embedded anti-insulin and the insulin antigen which is present in the medium.

TABLE 1

| | FIBRE | | TESTS | | | | |
|---|---|---|---|---|---|---|---|
| | Sample N° | Weight (mg) | Counts/10' 1° | Counts/10' 2° | Counts/10' 3° | Counts/10' 4° | Counts/10' 5° |
| Control series | $a_1$ | 7,0 | 6.822 | 5.059 | 2.703 | 2.579 | 2.718 |
| | $a_2$ | 12,5 | 12.716 | 11.162 | 5.567 | 4.966 | 5.127 |
| | $a_3$ | 18,4 | 15.328 | 3.405 | 5.132 | 5.543 | 6.314 |
| | $a_4$ | 25,0 | 16.060 | 16.595 | 6.594 | 6.983 | 7.059 |
| | $a_5$ | 33,7 | 15.317 | 20.919 | 9.564 | 8.474 | 7.915 |
| | $a_6$ | 41,8 | 22.412 | 22.695 | 11.668 | 11.960 | 10.396 |
| Antiserum-containing series | $b_1$ | 7,1 | 22.895 | 39.193 | 48.025 | 57.800 | 64.907 |
| | $b_2$ | 12,7 | 44.149 | 73.026 | 80.498 | 87.945 | 94.489 |
| | $b_3$ | 16,1 | 28.299 | 49.550 | 58.295 | 66.435 | 74.112 |
| | $b_4$ | 22,1 | 45.831 | 79.268 | 90.734 | 100.182 | 113.027 |
| | $b_5$ | 33,6 | 54.870 | 119.867 | 135.862 | 150.248 | 166.087 |
| | $b_6$ | 40,5 | 50.910 | 116.575 | 135.154 | 152.010 | 170.242 |
| Antiserum-containing series subjected to washing before use | $c_1$ | 9,8 | 32.593 | 52.763 | 67.770 | 74.800 | 85.678 |
| | $c_2$ | 11,3 | 39.403 | 65.432 | 79.011 | 84.292 | 91.836 |
| | $c_3$ | 12,3 | 43.554 | 66.607 | 83.098 | 97.018 | 107.592 |
| | $c_4$ | 12,1 | 42.794 | 68.325 | 82.292 | 94.203 | 105.739 |
| | $c_5$ | 40,1 | 50.883 | 104.108 | 121.027 | 132.263 | 148.442 |
| | $c_6$ | 42,7 | — | 66.490 | 89.960 | 99.300 | 111.166 |

TABLE 1-continued

| FIBRE | | TESTS | | | | |
|---|---|---|---|---|---|---|
| Sample N° | Weight (mg) | Counts/10' 1° | Counts/10' 2° | Counts/10' 3° | Counts/10' 4° | Counts/10' 5° |
| c₇ | 32,4 | — | 53.654 | 70.901 | 82.805 | 93.805 |

EXAMPLE 2

With the procedure as described above there was prepared, in Guinea pigs, an anti-HGH antiserum the entibody titre of which was found to be 2,000.

To 0.2 ml of this antiserum there was added 0.15 ml of 0.02 molar Veronal buffer, pH 8.4, containing 0.5% of human seroalbumin and 0.15 ml of glycerol (reagent grade, C. ERBA).

With the same apparatus as above there was performed the spinning of a control fibre, in which in place of 0.2 ml of antiserum solution use was made of 0.2 ml of 0.02 molar Veronal buffer, pH = 8.4, containing 0.5% of human seroalbumin.

In small plastic tubes of the kind of those used for the radioimmunoassays there were placed different amounts of fibres as reported in TABLE 2, wherein:

which contain the anti-HGH antibody, especially after the second test, there is, at all the concentration levels of added HGH, a quantity of fixed radioactivity which is greater with respect to the corresponding control fibres which do not contain antiserum in their interior, but which have been treated in very much the same way as those which have the antiserum embedded therein.

It should be noted that the anti-HGH antiserum used has a titre of 2,000 and thus the specific sequestering phenomenon is less conspicuous than that which was shown for the test reported in EXAMPLE 1, in which an anti-insulin antiserum was used, having a titre of 150,000.

The specific fixing due to the antigen-antibody bond in the fibres which contain the anti-HGH antibodies, is, however, unquestionable also in the case in point.

TABLE 2

| | FIBRE | | Concentration of the added standard HGH (micrograms/ml) | TESTS | |
|---|---|---|---|---|---|
| | Sample N° | weight (mg) | | Counts/10' 1° | counts/10' 2° |
| Control series | a₁ | 10,1 | 1,25 | 5.186 | 6.453 |
| | a₂ | 10,0 | 10 | 5.772 | 5.959 |
| | a₃ | 10,2 | 10 | 5,739 | 7.529 |
| | a₄ | 9,7 | — | 4.080 | 4.523 |
| | a₅ | 10,1 | 20 | 5.093 | 6.756 |
| | a₆ | 9,6 | — | 3.799 | 4.783 |
| | a₇ | 9,7 | 50 | 3.970 | 4.890 |
| | a₈ | 9,9 | — | 4.500 | 5.233 |
| Anti-serum containing series | b₁ | 9,6 | 1,25 | 6.239 | 9.169 |
| | b₂ | 10,4 | — | 6.029 | 9.492 |
| | b₃ | 10,2 | 10 | 6.266 | 9.112 |
| | b₄ | 10,5 | — | 5.616 | 8.779 |
| | b₅ | 10,0 | 20 | 5.259 | 7.739 |
| | b₆ | 10,2 | — | 5.653 | 8.163 |
| | b₇ | 9,8 | 50 | 4.943 | 6.736 |
| | b₈ | 9,8 | — | 5.366 | 7.899 | a. is the series of control fibres,
b. is the series of antiserum-containing fibres, as obtained from the spinning process, To the two series of small tubes (8 small tubes for each series) there was added:
- 1.6 ml of 0.13 molar borate buffer, pH = 8.4, containing 0.5% of BSA;
- 0.2 ml of HGH-I¹²⁵ with a specific activity of 150 μ Ci/microgram and with a dilution which brought the activity, as measured on the day of preparation, to 0.015 μ Ci/0.1 ml,
- 0.2 ml of standard HGH at the concentrations specified in TABLE 2.

After mixing, the small tubes were placed in a 4° C cabinet for 24 hours. Then, from each small tube there was taken off 1.5 ml of solution the radioactivity of which was measured with a gamma-counter (Packard, Model 256), having an efficiency of 54% for I¹²⁵.

The fibres were washed three times with 2 ml of borate buffer whereafter the radioactivity fixed in the fibres was measured with a gamma-counter as mentioned above. On the same fibre samples there were repeated once more the additions of the reagents (buffer, HGH-I¹²⁵, standard HGH), the washings and the radioactivity readings. The results obtained are reported in TABLE 2. It can be seen that, in the fibres

EXAMPLE 3

With the procedures as described above an antitriiodotyronine antiserum was prepared by inoculating in rabbits triiodotyronine (T₃) bonded to human seroalbumin. On the antiserum obtained there was determined an antibody titre of 4,000. To 0.2 ml of serum there was added 0.15 ml of 0.08 molar Veronal buffer, pH = 7.5, containing 0.5 g/liter of human seroalbumin and 0.15 ml of glycerol.

0.4 of the solution were embedded in 200 mg of cellulose triacetate according to the already described fibre preparation procedure.

With the same procedure a control fibre was prepared, in which, in the place of the antiserum solution there were embedded in 200 mg of cellulose triacetate 0.4 ml of a solution obtained by mixing 0.35 ml of 0.08 molar Veronal buffer, pH = 7.5, containing 0.5 g/liter of human seroalbumin and 0.15 ml glycerol.

50 mg of the antibody-containing fibre and 50 mg of the antibody devoid fibre were placed in two small tubes of plastic material and washed five times with 2 ml of the Veronal buffer described above.

Then, to each small tube, there was added:

2 ml of 0.08 molar Veronal buffer, pH = 7.5, containing 0.4 g/liter of human seroalbumin and 4 mg/liter of $T_3$.

0.2 ml of $T_3$-$I^{125}$ with a specific activity of 90 μ Ci/microgram diluted to an activity of 0.1 μ Ci/ml.

After mixing, the small tubes were placed in a 4° C cabinet for 24 hours.

Then the fibres were stripped of the solution containing the reagents and washed five times with 2 ml of the Veronal buffer described above.

Then the additions of the reagents and the washings were repeated for a second time, as specified above.

Lastly, the radioactivity present on the fibres was measured with the gamma-counter aforementioned.

On the fibre deprived of antibodies there were measured 45,000 counts/10': on the fibre which contained the antibody there were measured 146,000 counts/10'.

EXAMPLE 4

There was prepared with the already described procedures, an anti-light chain λ and K antibody at the concentration of 25 milligrams/milliliter in a physiological solution buffered to pH = 7.3 with 0.01 molar sodium phosphate.

To 0.35 ml of this solution there was added 0.15 ml of glycerol.

0.4 ml of the latter solution was embedded in 200 mg of cellulose triacetate with the already described procedure. By utilizing the same spinning procedure there was embedded in a control fibre 0.4 ml of the already described buffer.

100 mg of the antibody-containing fibre and 100 mg of the control fibre were placed in two small plastic tubes. The fibres were washed five times with 2 ml of 0.01 molar phosphate buffer, pH 7.3.

Then to the small tubes there was added 1 ml of 0.01 molar phosphate buffer, pH = 7.3, containing 0.9% of sodium chloride and 0.5 mg/ml of λ and K light chains.

The small tubes were kept for 2 hours at 22° C and for another 22 hours at 4° C.

After incubation, the solutions were taken from the small tubes and the fibres were washed five times with 1 ml of 0.01 molar phosphate buffer, pH = 7.3, containing 0.9% of sodium chloride.

The washing liquors were combined with the solutions taken from the tubes after incubation and on the solution thus obtained the proteinic concentration was determined with the Lowry method.

In the solutions which had been in contact with the control fibre there was measured 0.447 mg of proteins.

In the solutions which had been in contact with the antibody-containing fibre there was measured 0.385 of proteins.

What is claimed is:

1. A method for the preparation of porous fibres having microcavities containing antibody, antigen or antisera substances, and including selecting a spinning solvent and polymer which will not cause inactivation of the substances to be contained in said microcavities, comprising preparing the antibody, antigen or antisera substance to be embedded in the fibres and verifying the aspecific fixing of the substance on the material from which the fibres are to be made, and its lack of or non-significant inactivation, by treatment with the spinning solvents that are to be used in producing the fibres, mixing said substance with water or mixtures of glycerol and water, adding the mixture containing the substance to said polymer in solution, stirring until a homogeneous emulsion is obtained, spinning the emulsion through a spinneret immersed in a coagulation bath to produce porous fibres with said substance occluded within the microcavities in said fibres, and removing the coagulation liquor and the solvent of the polymer from the fibres by treatment thereof in a stream of air or other gas.

2. A method for the preparation of fibres as defined in claim 1, wherein said polymer is selected from cellulose polymers, esterified, etherified, or nitrated cellulose polymers.

3. A method for the preparation of fibers as defined in claim 1, wherein said polymer is polyethylene, polyamides, polymers or copolymers of acrylonitrile, butadiene or isoprene, acrylates, methacrylates, vinyl esters, vinyl chloride, the polymers and copolymers of vinylidene chloride, styrene, vinyl butyrate or gamma-methyl glutamate.

4. A polymeric structure comprising a porous artificial fibre made according to the process as defined in claim 1, wherein the substance occluded in the fibre is selected from the group consisting of antibodies, antigens and antisera, and the pores of said fibre are of such nature as to prevent escape of said occluded substance but to allow for the penetration of the agent that is to be reacted with said substance.

* * * * *